(12) United States Patent
Yoo et al.

(10) Patent No.: US 6,780,430 B2
(45) Date of Patent: Aug. 24, 2004

(54) STABILZATION METHOD OF NANO-SIZED EMULSION USING TOCOPHERYL DERIVATIVES AND EXTERNAL APPLICATION FOR SKIN CONTAINING THE SAME

(75) Inventors: Byung Hee Yoo, Suwon-shi (KR); Joung Soo Kim, Suwon-shi (KR); Byung Young Kang, Seoul (KR); Kil Joong Kim, Suwon-shi (KR); Sang Hoon Han, Suwon-shi (KR)

(73) Assignee: Pacific Corporation, Seoul (KR)

( * ) Notice: Subject to any disclaimer, the term of this patent is extended or adjusted under 35 U.S.C. 154(b) by 0 days.

(21) Appl. No.: 10/120,389

(22) Filed: Apr. 12, 2002

(65) Prior Publication Data

US 2003/0078238 A1 Apr. 24, 2003

(30) Foreign Application Priority Data

Jun. 5, 2001 (KR) ........................... 2001-31360

(51) Int. Cl.[7] ................. A61K 9/127; A61K 7/00; A61K 31/685
(52) U.S. Cl. .................. 424/450; 424/40; 424/401; 514/2; 514/78; 514/100
(58) Field of Search ............... 424/450, 400, 424/401; 514/78, 100, 2

(56) References Cited

U.S. PATENT DOCUMENTS 6,565,886 B1 * 5/2003 Simonnet et al. ........... 424/489

* cited by examiner

*Primary Examiner*—Shelley A. Dodson
(74) *Attorney, Agent, or Firm*—Nixon & Vanderhye P.C.

(57) ABSTRACT

Disclosed herein is a stabilization method of nano-sized emulsion by using lecithin and tocopheryl derivatives represented by the following formula (I) and (I)

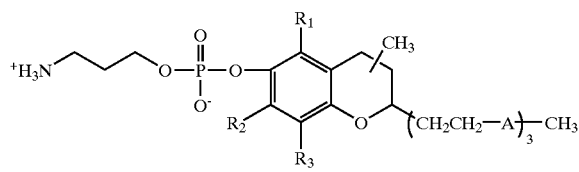

(Wherein,
$R_1$, $R_2$ and $R_3$ are H or methyl group, and at least one position selected from the group consisting of the $R_1$, $R_2$ and $R_3$ positions are methyl group; and,
A is $CH_2$—$CH(CH_3)$— or $CH$=$C(CH_3)$—)
and an external application for skin containing the stabilized nano-sized emulsion.

6 Claims, 1 Drawing Sheet

STABILZATION METHOD OF NANO-SIZED EMULSION USING TOCOPHERYL DERIVATIVES AND EXTERNAL APPLICATION FOR SKIN CONTAINING THE SAME

BACKGROUND OF THE INVENTION

1. Field of the Invention

The present invention relates to a stabilization method of nano-sized emulsion prepared by using lecithin as an emulsifier and to an external application for skin containing the stabilized nano-sized emulsion.

2. Description of the Prior Art

The skin, as the primary protect shield of the human body, shields the internal organs from the potentially damaging stimuli such as environmental changes, ultra violet rays, pollutants, etc. Recently, a lot of efforts have been undertaken to suppress aging of the skin and to maintain healthy and beautiful skin. For example, as an effort to maintain skin function and to suppress the aging and melanin accumulation of the skin, physiologically active materials obtained from animals, plants and microorganisms have been used as components of cosmetic compositions.

Especially, percutaneous methods for absorbing effective components directly through the skin have been much studied. Such percutaneous absorbing method is described below.

As a basic method, the physiologically active material is transferred into the skin by dissolving the active material in a suitable solvent and applying the solution to the skin. Therefore, the appropriate solvent for dissolving the active material should be selected. However, there are some problems that selecting the solvents complying with the active materials is difficult and that the selected solvents also cause irritation. Further, because it is difficult to control the usability, there are some difficulties in formulation of the cosmetic.

Following the above dissolving method, an emulsion-type percutaneous releasing agent to improve the usability and skin absorption has been developed. The technology has been developed from an early method of containing the active agent into micrometer-sized emulsion particles to a method of containing the active agent into the nanometer-sized emulsion particles. Specifically, a technology for preparing nanometer- or micrometer-sized emulsion particles using useful agents and lipids, glycerol, water, phospholipid or water-soluble non-ionic surfactants is disclosed in U.S. Pat. No. 5,338,761. Preparing nano-sized particles using a charged-lipid as an emulsifier is disclosed in U.S. Pat. No. 6,120,751. Further, a method for preparing nano-sized particles using micro-emulsions, that are obtained when three phases consisting of emulsifier, oil and water become balanced, is disclosed in U.S. Pat. No. 5,152,923, WO 91/06286 and WO 91/06287.

However, when an unstable active agent is contained in the emulsion particle, because the emulsion membrane kinetically equilibrates with the outer phase, the active agent continuously contacts the water, which causes oxidation and decomposition of the particles. Therefore, a lot of emulsifiers are needed to contain a sufficient amount of active agents, which may cause skin irritation.

To overcome the above problems, lecithin which has an excellent biocompatibility is used as an emulsifier in the preparation of nano-sized emulsion particles (U.S. Pat. Nos. 5,152,953 and 5,658,988).

However, when lecithin is used, because the lecithin has low physicochemical stability, the stability of the nano-sized emulsion particles prepared by using it becomes lower. Further, the stability of the active agents contained in the nano-sized emulsion particles is also low due to the instability of nano-sized emulsion particles.

The present inventors have conducted extensive studies on the method for stabilizing nano-sized emulsion particles using lecithin as emulsifier. As a result, they found that the lecithin-based nano-sized emulsion particles prepared by using tocopheryl derivatives together can achieve the stability of the emulsion particle itself, and also improve the stability of active agents contained in nano-sized emulsion particles. Based on this finding, the present invention is accomplished.

SUMMARY OF THE INVENTION

Thus, the purpose of the present invention is to provide a stabilization method of nano-sized emulsion particles prepared by using lecithin as emulsifier.

Further, another object of the present invention is to provide a nano-sized emulsion paticles stabilized by the foregoing method.

Also, still other object of the present invention is to provide an external composition for applying to the skin that contains the nano-sized emulsion particles.

The above and other objects and features of the present invention will be apparent to the skilled in the art from the following detailed description.

DETAILED DESCRIPTION OF THE INVENTION

Figure 1:
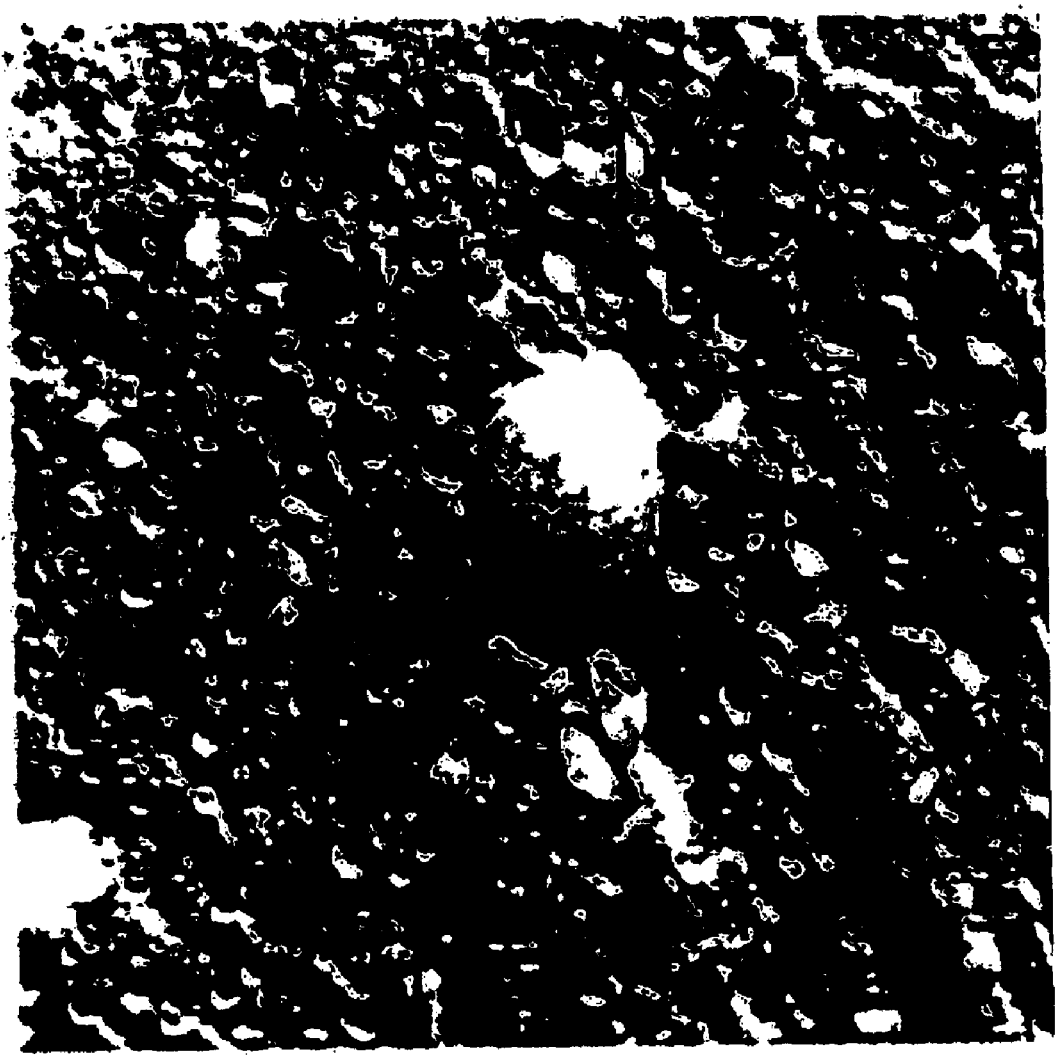
FIG. 1 is an enlarged photograph of the nano-sized emulsion particle of the present invention observed by transmission electron microscopy.

The present invention will be described in more detail hereinafter.

The stabilization method of nano-sized emulsion particles according to the present invention is characterized in that the tocopheryl derivatives represented by the following formula (I) are added in a ratio of 0.001~20 to the total amount of lecithin.

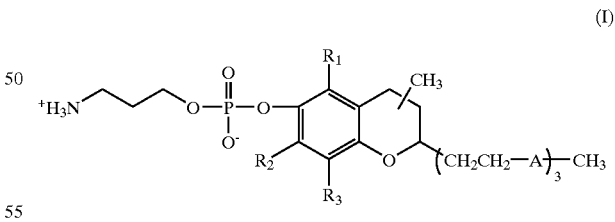

(Wherein,
  $R_1$, $R_2$ and $R_3$ are H or methyl group, and at least one selected from the group consisting of the $R_1$, $R_2$ and $R_3$ is methyl group; and,
  A is $CH_2$—$CH(CH_3)$— or $CH$=$C(CH_3)$—)

The present invention provides nano-sized emulsion particles having improved physicochemical stability by adding tocopheryl derivatives (I) while preparing nano-sized emulsion particles with lecithin. Further, the physiologically active agent is stably maintained in the above nano-sized emulsion particles.

The tocopheryl derivatives (I) used in the present invention do not cause an irritation to skin and have excellent anti-oxidant effect and stability in both water and lipid media because they possess both hydrophilic and lipophilic groups. These tocopheryl derivatives (I) are prepared; (A) by reacting tocopherol with phosphorous oxychloride at a temperature of −10° C. to 50° C. for 1~3 hours with an equivalent ratio of 1:1~1.3, in an organic solvent at presence of an organic base to produce tocopherol dichlorophosphate; (B) reacting the tocopherol dichlorophosphate produced by the above step (A) with 3-aminopropanol in an organic solvent at presence of an organic base to produce 2-tocopherol-tetrahydro-2H-1,3,2-oxazaphosphorin P-Oxide; (C) filtering the solution containing 2-tocopherol-tetrahydro-2H-1,3,2-oxazaphosphorin P-Oxide produced in step (B), and then adjusting the pH of filtrate to 1~5 and hydrolyzing the results at a temperature of 5~100° C., for 1~10 hours; and (D) extracting tocopheryl derivatives with an organic solvent and purifying them.

Using lecithin and tocopheryl derivatives in an adequate ratio stabilize the nano-sized emulsion particles of the present invention physicochemically. The size of the prepared nano-sized emulsion particles is 1~500 nm, preferably 30~150 nm. The nano-sized emulsion particle contains physiologically active materials therein. The active materials are instantaneously emitted in large quantities since the interfacial film of the particle is simultaneously destroyed by physical shearing force when the particles are applied to the skin. That is, when the particles are penetrated into skin and the external environments of the particles are changed to hydrophobic, the solubility of the lecithin and tocopheryl derivatives forming the interfacial film of the particle are increased, and thus the lecithin and tocopheryl derivatives are absorbed into phospholipid layer of intercellular, and as a result, the interfacial film of the particle is destroyed and the active materials contained in the particles are emitted in large quantities.

The physiologically active agent used in the nano-sized emulsion particles of the present invention may include, but not limited thereto, medicaments such as antibiotics, anti-tumor agent, anti-inflammatory agent, antipyretic, analgesia, anti-edema agent, anti-tussive agent, expectorant, depressant, muscle relaxant, antiepileptic, anti-ulcer agent, anti-melancholia agent, anti-allergy agent, cardiotonic agent, anti-arrhythmic agent, vasodilatin, hypotensive agent, anti-diabetic, homoeostasis agent, polypeptide, hormone; antioxidant; whitening agent; wrinkle prevention or removing agent such as collagen synthesizing accelerant, membrane fortifier and moisturizing agent.

More specifically physiologically active agent contained in the nano-particle includes, for example, antibiotics such as gentamicin, dibekacin, kanendomycin, lividomycin, tobramycin, amikacin, fradiomycin, sisomicin, tetracycline hydrochloride, oxytetracycline hydrochloride, rolitetracycline, doxycycline hydrochloride, ampicillin, piperacillin, ticarcillin, cephalothin, cephaloridine, cefotiam, cefsulodin, cefmenoxime, cefmetazole, cefazolin, cefotaxime, cefoperazone, ceftizoxime, moxolactam, latamoxef, thienamycin, sulfazecin and azthreonam; antitumor agents such as bleomycin hydrochloride, methotrexate, actinomycin D, mitomycin C, vinblastine sulfate, vincristine sulfate, daunorubicin hydrochloride, adriamycin, neocarcinostatin, cytosine arabinoside, fluorouracil, tetrahydrofuryl-5-fluorouracil, krestin, picibanil, lentinan, levamisole, bestatin, azimexon, glycyrrhizin, poly I:C, poly A:U and poly ICLC; anti-flamatory agents such as sodium salicylate, sulpyrine, sodium flufenamate, sodium diclofenac, sodium indomethacin, morphine hydrochloride, pethidine hydrochloride, levorphanol tartrate and oxymorphone; antiedemic agent; hormone medicaments such as lysozyme chloride and protein synthesis stimulating peptides; antioxidants such as coenzyme Q10(co-Q10), vineatrol (resvaratrol), BHT, vitamin A and its derivatives, vitamin C derivatives and vitamin E and its derivatives; antimicrobial agents such as tricolosan, chlorohexidine, cetylpyridinium chloride and natural essential oil; hair growth agents such as minoxidil, TGF (transforming growth factor), EGF (epidermal growth factor), FGF (fibroblast growth factor), IGF (insuline-like growth factor) testosterone and androgen; whitening agents; crease resistant and disapproval agent such as chollagen synthesizing accelerant; membrane fortifying and moisturizing agents such as ceramide and spingo acid; enzymes for corneous elemination such as papain, but the physiologically active agent is not limited thereto. The kinds and the amount of the active agents contained in the nano-particles are controlled according to the cases and the objects to be used.

Further, surfactants may be used to aid emulsifing ability of lecithin in preparation of the nano-sized emulsion particles. The surfactants used in the present invention may include, anionic surfactants such as higher fatty acid soap, sulfuric acid alkyl ester salts, polyoxyethylenealkylether sulfate, alkyl ether phosphoric acid ester salts and N-acylamino acid salts; cationic surfactants such as alkyltrimethyl ammounium chloride, dialkyldimethyl ammounium chloride and benzalkonium chloride; amphiphilic surfactants such as alkyldimethylamino acetic acid betaine, alkylamidedimethylaminoacetic acid betaine, and 2-alkyl-N-carboxy-N-hydroxyimidazolinium betaine; non-ionic surfactants such as polyoxyethylene-based surfactants, polyhydric alcohol ester-based surfactants and ethyleneoxide/propyleneoxide block copolyer; polymer surfactants such as ethylcellulose; natural surfactants such as lanolin, cholesterol, saponine and the like; but are not limited thereto, Further, soluble polymer may be added to improve the dispersion stability of the nano-sized cmulsion particles. The soluble polymer used in the present invention includes, natural polymers such as acacia gum, Irish moss, karaya gum, gum tragacanth, gum guaiac, xanthan gum and locust bean gum; proteins such as casein, gelatin, collagen, albumin (example, human serum albumin), globulin, fibrin and derivatives thereof; natural carbohydrates such as cellulose, dextrin, pectin, starch, agar, mannan and derivatives thereof; polyvinyl polymers and derivatives thereof such as polyvinylpyrrolidon, polyvinyl alcohol, polyvinylmethylether and polyvinylether, polycarboxylic acids and derivatives thereof such as polyacrylic acid, polymetacrylic acid and polymethylmetacrylate; hydrocarbons such as polyethylene, polypropylene and isomers thereof, and polysaccharide and its derivatives such as polysucrose, polyglucose, polylactose and salts thereof; but not limited thereto.

The amount of the lecithin and tocopheryl derivatives (I) used in preparation of nano-sized emulsion particles of the present invention depend on the kinds of active agents, slow-release, physical and chemical characteristics and so on. However, the amount of the lecithin is 0.1 to 100 times the weight of the active agent used, preferably 1 to 5 times the weight of the active agent used. The amount of tocopheryl derivatives (I) is 0.001 to 20 times the weight of the lecithin used, preferably 0.1 to 2 times the weight of the lecithin used.

The stabilized nano-sized emulsion particles of the present invention may be used preparation of external application composition. The external application composition may have a cosmetic formulation such as skin softner, nutrition lotion type emulsion, cleansing lotion, cleansing cream, skin milk, emollient lotion, massage cream, emollient cream, make-up base, lipstick, facial pack or facial gel, cleaner formulation such as shampoos, rinses, body cleanser, hair-tonics, or soaps, or dermatological composition such as lotions, ointments, gels, creams, patches or sprays.

PREFERRED EMBODIMENT OF THE INVENTION

The present invention will be described in more detail by the following examples. However, these examples are provided for only illustration purpose and should not be construed as limiting the scope of the invention, which is properly delineated in the accompanying claims.

The lecithins used in the following examples were "PHOSPHOLIPON 90" purchased from Nattennann Phopholipid GmbH. The ratio of phosphathidylcholin in the lecithin was 92.4% and the amount of lisophosphathidylcholin was 2.8%. The initial peroxide value of the lecithin was 3.3.

REFERENCE EXAMPLE 1

Preparation of 3-aminopropyl-α-tocopherol phosphate 9.87 g of phosphorus oxychloride (6.44 mmol) was placed in a round bottom flask and dissolved in 10 ml of tetrahydrofuran. Then, the resulting solution was cooled to 3° C. in an ice bath.

In another flask, the mixture solution of 21.54 g of α-tocopherol (5.00 mmol) and 6.10 g of triethylamine (6.03 mmol) was diluted with 40 ml of tetrahydrofuran. Then, the solution was added dropwisely to the above prepared phosphorus oxychloride solution for about 1 hour. After adding, the mixuture was stirred for about 30 minutes, and triethylamonnium chloride was removed through filtration. Then, the filtrate of tocopherol dichlorophosphate was cooled to 3° C. in an ice bath.

In another reactor, 3.76 g of 3-amino-1-propanol (5 mmol) and 11.11 g of triethylamine (10.98 mmol) were diluted with 20 ml of tetrahydrofuran. Then, the solution was added in drops to the above prepared filtrate for 1 hour to produce 2-tocopherol-tetrahydro-2H-1,3,2-oxazaphosporin P-oxide. After adding, the mixture was stirred for 30 minutes. Then, the reaction solution was filtrated to remove triethylammonium chloride. The filtrate was washed with sodium chloride solution, concentrated under reduced pressure. Thereafter, 40 ml of deionized water was added to the concentrated residue, then hydrochloric acid was added to adjust pH to 2. The reaction mixture was stirred at room temperature for about 2 hours, and washed by adding sodium chloride solution, then organic layer was separated. The organic layer was dehydrated with the aid of 10 g of anhydrous magnesium sulfate. After filtration, the solvent was removed completely, and 25 g of 3-aminopropyl-α-tocopherol phosphate was obtained in the yield of 88%.

$^1$H NMR(CDCl$_3$, 300 MHz); 0.86 (t, 12H), 1.00–1.80 (m, 29H), 2.01 (s, 3H), 2.11 (s, 3H), 2.15 (s, 3H), 2.40–2.50 (m, 2H), 2.70–2.80 (m, 2H), 3.90–4.00 (m, 2H), 7.80 (br, 3H)

EXAMPLES 1~24 AND COMPARATIVE EXAMPLES 1~4

Preparation of Nano-Sized Emulsion Particles

In order to determine an amount ratio of lecithin and tocopheryl derivatives in preparation of nano-sized emulsion particles, the nano-sized emulsion particles were prepared with varying the amount ratio of lecithin and tocopheryl derivatives without considering the active agents to be contained in the particles. Other surfactants and soluble polymer for stabilizing the dispersion were not used. The 2 g of lecithin and 0.02 g, 0.1 g, 0.2 g, 1.0 g, 2.0 g and 4.0 g of 0.13-aminopropyl-α-tocopherol phosphate of reference example 1 respectively were added into 10 g of cetylethylhexanoate and heated in 60° C. to obtain homogenous solubility. To mixture added the distilled water to be total amount of 200 g. For the first emulsifying, the above mixture was treated by the homogenizer at 5,000 rpm for 3 minutes, then treated three times using the microfluidizer (high pressure homogenizer) to prepare nanometer-sized emulsion particles of Examples 1~6 and Comparative Example 1.

In order to confirm the stability of active agent contained the nano-sized emulsion particles, the nano-sized emulsion particles containing retinol, coenzyme-Q10 and resveratrol as the active agent were prepared. That is to say, 0.5 g of the active agent was respectively added into cetylethylhaxanoate. Then, 2 g of lecithin and 0.02 g, 0.1 g, 0.2 g, 1.0 g, 2.0 g and 4.0 g of 0.13-aminopropyl-α-tocopherol phosphate of reference example 1 respectively were added into the mixture and heated in 60° C. to obtain homogenous solubility. To the mixture was added the distilled water to be total amount of 200 g. For the first emulsification, the above mixture was treated by the homogenizer at 5,000 rpm for 3 minutes, then treated three times using the microfluidizer (high pressure homogenizer) to prepare the nanometer-sized emulsion particles containing the physiological active agents of Examples 7~24 and Comparative Example 2~4.

Diameter distribution of the nano particles prepared in the above example was measured by dynamic laser light scattering method (Zetasizer 3000HS, Malvern, UK). The scattering angle was fixed at 90°, and the temperature was fixed at 25° C. The relationship between the diameter of the particle and polydispersity was calculated by the "contin" method. In the meantime, if the visual method is used by cohesion and precipitation, the diameter of the particles are not separately measured. The prepared nano-sized emulsion particles are classified in Table 1.

TABLE 1

| Nano-sized emulsion particles | Physical active agent* | Lecithin/Tocopheryl derivatives* | Mean diameter (nm) |
|---|---|---|---|
| Example 1 | Not contained | 1/0.01 | 35 |
| Example 2 | | 1/0.05 | 38 |
| Example 3 | | 1/0.10 | 42 |
| Example 4 | | 1/0.50 | 45 |
| Example 5 | | 1/1.00 | 48 |
| Example 6 | | 1/2.00 | 51 |
| Comparative Example 1 | | 1/0.00 | 39 |
| Example 7 | Retinol | 1/0.01 | 36 |
| Example 8 | (0.25) | 1/0.05 | 38 |
| Example 9 | | 1/0.10 | 41 |
| Example 10 | | 1/0.50 | 44 |
| Example 11 | | 1/1.00 | 45 |
| Example 12 | | 1/2.00 | 48 |
| Comparative Example 2 | | 1/0.00 | 42 |
| Example 13 | Coenzyme-Q10 | 1/0.01 | 32 |
| Example 14 | (0.25) | 1/0.05 | 35 |
| Example 15 | | 1/0.10 | 39 |
| Example 16 | | 1/0.50 | 44 |
| Example 17 | | 1/1.00 | 49 |
| Example 18 | | 1/2.00 | 53 |

TABLE 1-continued

| Nano-sized emulsion particles | Physical active agent* | Lecithin/Tocopheryl derivatives* | Mean diameter (nm) |
|---|---|---|---|
| Comparative Example 3 | | 1/0.00 | 40 |
| Example 19 | Resveratrol | 1/0.01 | 33 |
| Example 20 | (0.25) | 1/0.05 | 36 |
| Example 21 | | 1/0.10 | 40 |
| Example 22 | | 1/0.50 | 44 |
| Example 23 | | 1/1.00 | 47 |
| Example 24 | | 1/2.00 | 52 |
| Comparative Example 4 | | 1/0.00 | 41 |

*The amount of physiological active agent and the amount ration of lecithin and tocopheryl derivatives mean the mass ratio based on the total emulsion.

EXPERIMENTAL EXAMPLE 1

In order to confirm the preparation of the nano-sized emulsion particles, the samples are observed with transmission electron microscopy. The measurement method is as follows; 10~20 µl of sample (Example 10) was inserted in copper holder and quenched with Liquid Nitrogen Zet Condenser (Polaron, UK). The quenched sample was cut to expose the section of the sample and negative straining was carried out with a small portion of 2% ammoniummolybdenate solution. Then, it was stuck to a carbon thin film and observed with Jeol 100CX II transmission electron microscopy. An enlarged photograph of 90,000 times of the nano-sized emulsion particle was observed by the aforementioned method Results obtained by observing Example 1 are shown in FIG. 1.

In FIG. 1, a small circle shape shows the nano-sized emulsion and large circle particles show the emulsion having a relatively large diameter formed in the preparation of the nano-sized emulsion particle.

EXPERIMENTAL EXAMPLE 2

Stability of the Nano-Sized Emulsion Particles

In order to confirm stability of the nano-sized emulsion particles, the nano-sized emulsion particle samples obtained in each of the examples were stored in thermostatic baths with the temperatures of 0° C., 25° C., 37° C. and 45° C. After 30 days, the dispersion stability and emulsion stability of the particles were measured. Diameter variation of the particles was measured by dynamic laser light scattering method used in Example. If cohesion and precipitation is observed by the naked eye, the diameters of the particles are not separately measured. The results are shown in Table 2.

TABLE 2

| | 0° C. | 25° C. | 37° C. | 45° C. |
|---|---|---|---|---|
| Example 1 | Δ | Δ | x | x |
| Example 2 | 0 | 0 | Δ | Δ |
| Example 3 | 0 | 0 | 0 | 0 |
| Example 4 | 0 | 0 | 0 | 0 |
| Example 5 | 0 | 0 | 0 | 0 |
| Example 6 | 0 | 0 | 0 | 0 |
| Comparative Example 1 | xx | xxx | xxx | xxx |
| Example 7 | 0 | Δ | Δ | Δ |
| Example 8 | 0 | 0 | Δ | Δ |
| Example 9 | 0 | 0 | 0 | Δ |
| Example 10 | 0 | 0 | 0 | 0 |
| Example 11 | 0 | 0 | 0 | 0 |
| Example 12 | 0 | 0 | 0 | 0 |
| Comparative Example 2 | xx | xxx | xxx | xxx |
| Example 13 | 0 | Δ | Δ | Δ |
| Example 14 | 0 | 0 | Δ | Δ |
| Example 15 | 0 | 0 | 0 | Δ |
| Example 16 | 0 | 0 | 0 | 0 |
| Example 17 | 0 | 0 | 0 | 0 |
| Example 18 | 0 | 0 | 0 | 0 |
| Comparative Example 3 | xx | xxx | xxx | xxx |
| Example 19 | 0 | Δ | Δ | Δ |
| Example 20 | 0 | 0 | 0 | Δ |
| Example 21 | 0 | 0 | 0 | 0 |
| Example 22 | 0 | 0 | 0 | 0 |
| Example 23 | 0 | 0 | 0 | 0 |
| Example 24 | 0 | 0 | 0 | 0 |
| Comparative Example 4 | xx | xxx | xxx | xxx |

0: The variation of diameter is less than 50% based on the early diameter
Δ: The variation of diameter is less than 50~100% based on the early diameter
x: The variation of diameter is over 100% based on the early diameter
xx: The particles were visible to the naked eye by cohesion and precipitation
xxx: layer separation As shown in Table 2, when the emulsion was carried out with only lecithin (Comparative Example 1~4), the stability of the emulsion is very low and the particles could be seen by the naked eye by cohesion and precipitation were formed. When the emulsion was carried out with lecithin and tocopheryl derivatives (Example 1~24), the emulsion was dispersed physically stable for a lone time.

The formulation of cosmetics containing the nano-sized emulsion particles prepared by the aforementioned method are shown as follows.

<Formulations 1~3 and Comparative Formulations 1~3> Cream

| Materials | Formulations | | | C. Formulations | | |
|---|---|---|---|---|---|---|
| | 1 | 2 | 3 | 1 | 2 | 3 |
| Bees-wax | 2.0 | 2.0 | 2.0 | 2.0 | 2.0 | 2.0 |
| Glycerolstearate | 2.5 | 2.5 | 2.5 | 2.5 | 2.5 | 2.5 |
| Cetostearate | 1.5 | 1.5 | 1.5 | 1.5 | 1.5 | 1.5 |
| Polysolbate 60 | 0.5 | 0.5 | 0.5 | 0.5 | 0.5 | 0.5 |
| Solvitancesquiolate | 5.0 | 5.0 | 5.0 | 5.0 | 5.0 | 5.0 |
| Cethylethylhexanoate | 5.0 | 5.0 | 5.0 | 5.0 | 5.0 | 5.0 |
| Squalane | 8.0 | 8.0 | 8.0 | 8.0 | 8.0 | 8.0 |
| Liquid paraffin | 8.0 | 8.0 | 8.0 | 8.0 | 8.0 | 8.0 |

-continued

| | | | | | | |
|---|---|---|---|---|---|---|
| Glycerin | 4.0 | 4.0 | 4.0 | 4.0 | 4.0 | 4.0 |
| Propyleneglycol | 5.0 | 5.0 | 5.0 | 5.0. | 5.0 | 5.0 |
| Example 10 | 5.0 | — | — | — | — | — |
| Example 16 | — | 5.0 | — | — | — | — |
| Example 22 | — | — | 5.0 | — | — | — |
| Comparative Example 2 | — | — | — | 5.0 | — | — |
| Comparative Example 3 | — | — | — | — | 5.0 | — |
| Comparative Example 4 | — | — | — | — | — | 5.0 |
| Plant extracts | a.q | a.q | a.q | a.q | a.q | a.q |
| Preservative | a.q | a.q | a.q | a.q | a.q | a.q |
| Perfume | a.q | a.q | a.q | a.q | a.q | a.q |
| Pigment | a.q | a.q | a.q | a.q | a.q | a.q |
| Distilled water | to 100 | to 100 | to 100 | to 100 | to 100 | to 100 |

<Formaulations 4~6 and Comparative Formulations 4~6> Nutrition lotion type emulsion

| | Formulations | | | C. Formulations | | |
|---|---|---|---|---|---|---|
| Materials | 4 | 5 | 6 | 4 | 5 | 6 |
| Cetylethylhexanoate | 5.0 | 5.0 | 5.0 | 5.0 | 5.0 | 5.0 |
| Cetostearylalcohol | 1.0 | 1.0 | 1.0 | 1.0 | 1.0 | 1.0 |
| Lipophilicmonostearic acid stearate | 0.8 | 0.8 | 0.8 | 0.8 | 0.8 | 0.8 |
| Squalane | 2.0 | 2.0 | 2.0 | 2.0 | 2.0 | 2.0 |
| Polysolbate 60 | 1.5 | 1.5 | 1.5 | 1.5 | 1.5 | 1.5 |
| Solbitancesquiolate | 0.5 | 0.5 | 0.5 | 0.5 | 0.5 | 0.5 |
| Example 10 | 5.0 | — | — | — | — | — |
| Example 16 | — | 5.0 | — | — | — | — |
| Example 22 | — | — | 5.0 | — | — | — |
| Comparative Example 2 | — | — | — | 5.0 | — | — |
| Comparative Example 3 | — | — | — | — | 0.5 | — |
| Comparative Example 4 | — | — | — | — | — | 0.5 |
| Glycerin | 8.0 | 8.0 | 8.0 | 8.0 | 8.0 | 8.0 |
| Triethanol amine | 0.2 | 0.2 | 0.2 | 0.2 | 0.2 | 0.2 |
| Carboxyvinyl polymer | 0.2 | 0.2 | 0.2 | 0.2 | 0.2 | 0.2 |
| Preservative | a.q | a.q | a.q | a.q | a.q | a.q |
| Perfume | a.q | a.q | a.q | a.q | a.q | a.q |
| Pigment | a.q | a.q | a.q | a.q | a.q | a.q |
| Distilled water | to 100 | to 100 | to 100 | to 100 | to 100 | to 100 |

<Formulations 7~9 and Comparative Formulations 7~9> Skin softener

| | Formulations | | | C. Formulations | | |
|---|---|---|---|---|---|---|
| Materials | 7 | 8 | 9 | 7 | 8 | 9 |
| Betain | 3.0 | 3.0 | 3.0 | 3.0 | 3.0 | 3.0 |
| Natto gum | 3.0 | 3.0 | 3.0 | 3.0 | 3.0 | 3.0 |
| Cellulose gum | 0.08 | 0.08 | 0.08 | 0.08 | 0.08 | 0.08 |
| Ethanol | 5.0 | 5.0 | 5.0 | 5.0 | 5.0 | 5.0 |
| Polyoxyethylenerigid castor oil | 0.5 | 0.5 | 0.5 | 0.5 | 0.5 | 0.5 |
| Tocopherol acetate | 0.2 | 0.2 | 0.2 | 0.2 | 0.2 | 0.2 |
| Example 10 | 5.0 | — | — | — | — | — |
| Example 16 | — | 5.0 | — | — | — | — |
| Example 22 | — | — | 5.0 | — | — | — |
| Comparative Example 2 | — | — | — | 5.0 | — | — |
| Comparative Example 3 | — | — | — | — | 5.0 | — |
| Comparative Example 4 | — | — | — | — | — | 5.0 |
| Preservative | a.q | a.q | a.q | a.q | a.q | a.q |
| Pigment | a.q | a.q | a.q | a.q | a.q | a.q |
| Distilled Water | to 100 | to 100 | to 100 | to 100 | to 100 | to 100 |

<Formulations 10~12 and Comparative Formulations 10~12> Gel

| | Formulations | | | C. Formulations | | |
|---|---|---|---|---|---|---|
| Materials | 10 | 11 | 12 | 10 | 11 | 12 |
| Disodiumethylenediaminetetraacetate | 0.02 | 0.02 | 0.02 | 0.02 | 0.02 | 0.02 |
| Etoxyglycol | 1.0 | 1.0 | 1.0 | 1.0 | 1.0 | 1.0 |
| Polyacrylate | 20.00 | 20.00 | 20.00 | 20.00 | 20.00 | 20.00 |
| Ethanol | 30.00 | 30.00 | 30.00 | 30.00 | 30.00 | 30.00 |
| Example 10 | 5.0 | — | — | — | — | — |
| Example 16 | — | 5.0 | — | — | — | — |
| Example 22 | — | — | 5.0 | — | — | — |
| Comparative Example 2 | — | — | — | 5.0 | — | — |
| Comparative Example 3 | — | — | — | — | 5.0 | — |
| Comparative Example 4 | — | — | — | — | — | 5.0 |
| Hydrogenated castor oil | 0.80 | 0.80 | 0.80 | 0.80 | 0.80 | 0.80 |

-continued

| | | | | | | |
|---|---|---|---|---|---|---|
| Phenyltrimethicon | 0.20 | 0.20 | 0.20 | 0.20 | 0.20 | 0.20 |
| Triethanolamine | 0.40 | 0.40 | 0.40 | 0.40 | 0.40 | 0.40 |
| Perfume | a.q | a.q | a.q | a.q | a.q | a.q |
| Distilled water | to 100 | to 100 | to 100 | to 100 | to 100 | to 100 |

<Formulations 13~15 and Comparative Formulations 13~15> Spray

| | Formulations | | | C. Formulations | | |
|---|---|---|---|---|---|---|
| Materials | 13 | 14 | 15 | 13 | 14 | 15 |
| Triethanolamine | 0.2 | 0.2 | 0.2 | 0.2 | 0.2 | 0.2 |
| Polyvinylpyrrolidon/vinylacetate | 3.0 | 3.0 | 3.0 | 3.0 | 3.0 | 3.0 |
| Example 3 | 5.0 | — | — | 5.0 | 5.0 | 5.0 |
| Example 6 | — | 5.0 | — | — | — | — |
| Example 8 | — | — | 5.0 | — | — | — |
| Comparative Example 2 | — | — | — | 5.0 | — | — |
| Comparative Example 3 | — | — | — | — | 5.0 | — |
| Comparative Example 4 | — | — | — | — | — | 5.0 |
| Glycerine | 5.0 | 5.0 | 5.0 | 5.0 | 5.0 | 5.0 |
| Polyacrylate | 0.2 | 0.2 | 0.2 | 0.2 | 0.2 | 0.2 |
| Distilled water | to 100 | to 100 | to 100 | to 100 | to 100 | to 100 |

<Formulations 16~18 and Comparative Formulations 16~18> Ointment

| | Formulations | | | C. Formulations | | |
|---|---|---|---|---|---|---|
| Materials | 15 | 16 | 17 | 15 | 16 | 17 |
| Caprin/capryltglyceride | 10.0 | 10.0 | 10.0 | 10.0 | 10.0 | 10.0 |
| Liquid paraffin | 10.0 | 10.0 | 10.0 | 10.0 | 10.0 | 10.0 |
| Solbitancesquioliate | 6.0 | 6.0 | 6.0 | 6.0 | 6.0 | 6.0 |
| Octyldodeces-25 | 9.0 | 9.0 | 9.0 | 9.0 | 9.0 | 9.0 |
| Cethylehtylhexanoate | 10.0 | 10.0 | 10.0 | 10.0 | 10.0 | 10.0 |
| Squalane | 1.0 | 1.0 | 1.0 | 1.0 | 1.0 | 1.0 |
| Glycerin | 15.0 | 15.0 | 15.0 | 15.0 | 15.0 | 15.0 |
| Solibitol | 10.0 | 10.0 | 10.0 | 10.0 | 10.0 | 10.0 |
| Example 3 | 5.0 | — | — | — | — | — |
| Example 6 | — | 5.0 | — | — | — | — |
| Example 8 | — | — | 5.0 | — | — | — |
| Comparative Example 2 | — | — | — | 5.0 | — | — |
| Comparative Example 3 | — | — | — | — | 5.0 | — |
| Comparative Example 4 | — | — | — | — | — | 5.0 |
| Distilled water | to 100 | to 100 | to 100 | to 100 | to 100 | to 100 |

<Formulations 19~21 and Comparative Formulations 19~21> Patch

| | Formulations | | | C. Formulations | | |
|---|---|---|---|---|---|---|
| Materials | 19 | 20 | 21 | 19 | 20 | 21 |
| Polyvinylalcohol | 2.0 | 2.0 | 2.0 | 2.0 | 2.0 | 2.0 |
| Polyvinyl pyrrolidon | 3.0 | 3.0 | 3.0 | 3.0 | 3.0 | 3.0 |
| Sodium polyacrylate | 3.0 | 3.0 | 3.0 | 3.0 | 3.0 | 3.0 |
| Sodium algenate | 1.0 | 1.0 | 1.0 | 1.0 | 1.0 | 1.0 |
| Retinylpalmitate | 1.0 | 1.0 | 1.0 | 1.0 | 1.0 | 1.0 |
| Butyleneglycol | 3.0 | 3.0 | 3.0 | 3.0 | 3.0 | 3.0 |
| Chondroitin sulfate | 1.0 | 1.0 | 1.0 | 1.0 | 1.0 | 1.0 |
| *Schizophyllum coummune* extract | 1.0 | 1.0 | 1.0 | 1.0 | 1.0 | 1.0 |
| Medofoam oil | 1.0 | 1.0 | 1.0 | 1.0 | 1.0 | 1.0 |
| PEG(20) solbitanstearate | 1.0 | 1.0 | 1.0 | 1.0 | 1.0 | 1.0 |
| BHT | a.q | a.q | a.q | a.q | a.q | a.q |
| Zinc oxide | a.q | a.q | a.q | a.q | a.q | a.q |
| Example 10 | 5.0 | — | — | — | — | — |
| Example 16 | — | 5.0 | — | — | — | — |
| Example 22 | — | — | 5.0 | — | — | — |
| Comparative Example 2 | — | — | — | 5.0 | — | — |
| Comparative Example 3 | — | — | — | — | 5.0 | — |
| Comparative Example 4 | — | — | — | — | — | 5.0 |
| Distilled water | to 100 | to 100 | to 100 | to 100 | to 100 | to 100 |

Experimental Example 3

Stability test of the active agents contained in nano particles

The stability of the active agents contained in nano particles according to the storage term was observed with high performance liquid chromatography. The initial amount of the active agent is regarded as 100, then the relative amount of the active agent remaining with time is calculated. Samples were stored in thermostatic baths with the temperatures of 25° C. The results of nano-sized emulsion particles are shown in Table 3 and the results of formulations are shown in Table 4.

The analysis conditions of respective agent are as follows.

<Quantitative Analysis Conditions of Retinol>

Column: C18 (4.6×250 mm, 5 m)

Moving phase: methanol or ethanol 93%

Flow rate: 0.8 ml/min

Detector: UV 325 nm

<Quantitative Analysis Conditions of Coenzyme-Q10>

Column: Ubondapak C18 (3.9×150 mm)

Moving phase: methanol/ethanol (40/60)

Flow rate: 1 ml/min

Detector: UV 275 nm

<Quantitative Analysis Conditions of Resveratrol>

Column: MyghtySil ODS (4.6×250 mm, 5 m)

Moving phase: acetonitile/10 mM phosphate buffer solution

Flow rate: 1.0 ml/min

Detector: UV 252 nm

TABLE 3

| Particles | Initial | 7-days | 30 days | 60 days |
|---|---|---|---|---|
| Example 7 | 100% | 97 | 92 | 80 |
| Example 8 | 100% | 97 | 95 | 85 |
| Example 9 | 100% | 98 | 96 | 93 |
| Example 10 | 100% | 99 | 97 | 95 |
| Example 11 | 100% | 99 | 98 | 96 |
| Example 12 | 100% | 99 | 98 | 98 |
| C. Example 2 | 100% | 94 | 83 | 71 |
| Example 13 | 100% | 97 | 90 | 82 |
| Example 14 | 100% | 97 | 94 | 91 |
| Example 15 | 100% | 97 | 96 | 93 |
| Example 16 | 100% | 98 | 96 | 95 |
| Example 17 | 100% | 98 | 97 | 96 |
| Example 18 | 100% | 99 | 98 | 98 |
| C. Example 3 | 100% | 93 | 81 | 69 |
| Example 19 | 100% | 97 | 93 | 85 |
| Example 20 | 100% | 97 | 95 | 90 |
| Example 21 | 100% | 97 | 95 | 94 |
| Example 22 | 100% | 98 | 96 | 95 |
| Example 23 | 100% | 98 | 97 | 96 |
| Example 24 | 100% | 98 | 97 | 97 |
| C. Example 4 | 100% | 92 | 82 | 65 |

From the above results, when the particle were prepared with only lecithin (Comparative Example 2~4), the amount of the active agents contained in the particles sharply decreased in storage conditions of 25° C. However, when the particles was carried out with lecithin and tocopheryl derivatives (Example 7~24), the active agents were stably stored for a lone time. Because lecithin and tocopheryl derivatives formed a tight structure with each other, it prevented the water from being dispersed into the particles and therefore inner active agents did not come in contact with the water.

TABLE 4

| | | Initial | 7 days | 30 days | 60 days |
|---|---|---|---|---|---|
| Formulation | 1 | 100% | 98 | 96 | 92 |
| | 2 | 100% | 99 | 97 | 91 |
| | 3 | 100% | 98 | 96 | 92 |
| | 4 | 100% | 97 | 96 | 93 |
| | 5 | 100% | 99 | 97 | 92 |
| | 6 | 100% | 98 | 95 | 94 |
| | 7 | 100% | 99 | 96 | 93 |
| | 8 | 100% | 98 | 96 | 92 |
| | 9 | 100% | 98 | 97 | 93 |
| | 10 | 100% | 99 | 96 | 94 |
| | 11 | 100% | 99 | 97 | 93 |
| | 12 | 100% | 99 | 96 | 95 |
| | 13 | 100% | 98 | 97 | 93 |
| | 14 | 100% | 97 | 97 | 94 |
| | 15 | 100% | 98 | 98 | 96 |
| | 16 | 100% | 98 | 96 | 95 |
| | 17 | 100% | 99 | 95 | 93 |
| | 18 | 100% | 99 | 96 | 94 |
| | 19 | 100% | 99 | 97 | 96 |
| | 20 | 100% | 98 | 96 | 96 |
| | 21 | 100% | 98 | 95 | 95 |
| Comparative formulation | 1 | 100% | 93 | 81 | 66 |
| | 2 | 100% | 90 | 84 | 65 |
| | 3 | 100% | 91 | 82 | 67 |
| | 4 | 100% | 92 | 79 | 62 |
| | 5 | 100% | 93 | 76 | 58 |
| | 6 | 100% | 92 | 81 | 60 |
| | 7 | 100% | 90 | 82 | 61 |
| | 8 | 100% | 92 | 82 | 59 |
| | 9 | 100% | 91 | 78 | 53 |
| | 10 | 100% | 90 | 80 | 58 |
| | 11 | 100% | 89 | 49 | 54 |
| | 12 | 100% | 89 | 82 | 59 |
| | 13 | 100% | 88 | 75 | 53 |
| | 14 | 100% | 91 | 80 | 52 |
| | 15 | 100% | 92 | 76 | 53 |
| | 16 | 100% | 90 | 77 | 51 |
| | 17 | 100% | 83 | 80 | 65 |
| | 18 | 100% | 91 | 46 | 53 |
| | 19 | 100% | 93 | 83 | 68 |
| | 20 | 100% | 92 | 81 | 64 |
| | 21 | 100% | 90 | 79 | 63 |

As shown in Table 4, the active agents contained in the nano-sized emulsion particles were stabilized in formulations. It is expected that the particles will form multiple emulsion shapes in the formulation. As a result, the particles will be in less contact with water, thus the active agents are stabilized.

EXPERIMENTAL EXAMPLE 4

Safety onto the Skin

In order to evaluate the safety of the nano-sized emulsion particles and the formulation containing the particles, the conventional patch test was carried out for samples prepared in Examples 1~24, Comparative Examples 1~4 and Formulations 1~24 in fifty healthy males or females for 7 days, and the level of skin irritation was estimated according to the scoring system of the following Table 5 after 1 day, 3 days and 7 days.

TABLE 5

| | |
|---|---|
| 4 | Extremely severe(erythema, edema) |
| 3 | Severe irritation(erythema, edema) |
| 2 | A little irritation(erythema) |
| 1 | Little irritation(barely feeling) |
| 0 | No irritation |

Average degree value of the irritation was calculated by summing up the degree of the each person then dividing the sum with the number of the persons. The results are shown in Table 6.

TABLE 6

| Samples | Degree of the irritation % | | |
|---|---|---|---|
| | 1 day | 3 days | 7 days |
| Example 1 | 0.5 | 0.5 | 0.8 |
| Example 2 | 0.6 | 0.7 | 0.5 |
| Example 3 | 0.5 | 0.5 | 0.4 |
| Example 4 | 0.7 | 0.5 | 0.6 |
| Example 5 | 0.5 | 0.6 | 0.7 |
| Example 6 | 0.2 | 0.5 | 0.5 |
| C. Example 1 | 0.3 | 0.4 | 0.8 |
| Example 7 | 0.4 | 0.5 | 0.6 |
| Example 8 | 0.1 | 0.4 | 0.4 |
| Example 9 | 0.2 | 0.3 | 0.2 |
| Example 10 | 0.3 | 0.1 | 0.7 |
| Example 11 | 0.5 | 0.5 | 0.5 |
| Example 12 | 0.1 | 0.8 | 0.4 |
| C. Example 2 | 0.3 | 0.9 | 0.8 |
| Example 13 | 0.4 | 0.6 | 0.5 |
| Example 14 | 0.6 | 0.7 | 0.6 |
| Example 15 | 0.5 | 0.5 | 0.5 |
| Example 16 | 0.4 | 0.4 | 0.6 |
| Example 17 | 0.3 | 0.5 | 0.4 |
| Example 18 | 0.2 | 0.8 | 0.7 |
| C. Example 3 | 0.5 | 0.7 | 0.5 |
| Example 19 | 0.4 | 0.7 | 0.8 |
| Example 20 | 0.6 | 0.5 | 0.6 |
| Example 21 | 0.5 | 0.3 | 0.5 |
| Example 22 | 0.3 | 0.5 | 0.4 |
| Example 23 | 0.2 | 0.8 | 0.8 |
| Example 24 | 0.4 | 0.6 | 0.7 |
| C. Example 4 | 0.2 | 0.4 | 0.5 |
| Formulation 1 | 0.2 | 0.4 | 0.6 |
| Formulation 2 | 0.1 | 0.5 | 0.5 |
| Formulation 3 | 0.3 | 0.6 | 0.4 |
| Formulation 4 | 0.2 | 0.4 | 0.3 |
| Formulation 5 | 0.3 | 0.5 | 0.5 |
| Formulation 6 | 0.2 | 0.3 | 0.6 |
| Formulation 7 | 0.3 | 0.5 | 0.5 |
| Formulation 8 | 0.4 | 0.4 | 0.6 |
| Formulation 9 | 0.2 | 0.5 | 0.5 |
| Formulation 10 | 0.3 | 0.3 | 0.4 |
| Formulation 11 | 0.4 | 0.4 | 0.5 |
| Formulation 12 | 0.3 | 0.3 | 0.6 |
| Formulation 13 | 0.2 | 0.3 | 0.4 |
| Formulation 14 | 0.1 | 0.4 | 0.5 |
| Formulation 15 | 0.3 | 0.4 | 0.6 |
| Formulation 16 | 0.3 | 0.3 | 0.4 |
| Formulation 17 | 0.2 | 0.3 | 0.5 |
| Formulation 18 | 0.3 | 0.4 | 0.5 |
| Formulation 19 | 0.3 | 0.5 | 0.6 |
| Formulation 20 | 0.2 | 0.4 | 0.5 |
| Formulation 21 | 0.4 | 0.4 | 0.6 |

In all samples of Examples 1 to 24 and Comparative Examples 1 to 4, no significant irritation was felt. In addition, the cosmetic and medical compositions containing the active agents prepared in Formulations 1 to 21 did not cause skin irritation.

From the results above, it is sure that the nano-sized emulsion particles containing active agent prepared in the present invention show high affinity to the skin and the active agents can be formulated without causing skin irritation.

What is claimed is:

1. A method for stabilizing a nano-sized emulsion particle prepared by using lecithin, in which a tocopheryl derivative represented by the following formula (I) is further added to stabilize the emulsion particle in a ratio of 0.001~to 20 to the total amount of lecithin when the particle is prepared:

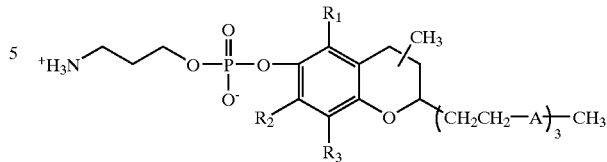

wherein,
from $R_1$, $R_2$ and $R_3$ are H or methyl groups, respectively, and at least one selected the group consisting of the $R_1$, $R_2$ and $R_3$ is methyl group; and
A is $CH_2$—$CH(CH_3)$—or $CH$=$C(CH_3)$—.

2. The method according to claim 1, wherein said nano-sized particle contains physiologically active agents therein.

3. The method according to claim 2, wherein said physiologically active agent is at least one member selected from the group consisting of antibiotics, anti-tumor agent, anti-inflammatory agent, antipyretic, analgesia, anti-edema agent, anti-tussive agent, expectorant, depressant, muscle relaxant, antiepileptic, anti-ulcer agent, anti-melancholia agent, anti-allergy agent, cardiotonic agent, anti-arrhythmic agent, vasodilatin, hypotensive agent, anti-diabetic, homoeostasis agent, polypeptide, hormone; antioxidant; whitening agent, collagen synthesizing accelerant, membrane fortifier, moisturizing agent and an enzyme for removing a stratum corneum.

4. A composition for external application to the skin comprising nano-sized emulsion particles prepared by lecithin and a tocopheryl derivative represented by the following formula (I):

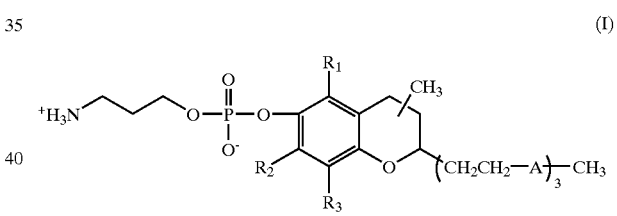

wherein,
$R_1$, $R_2$ and $R_3$ are H or methyl group respectively, and at least one selected from the group consisting of the $R_1$, $R_2$ and $R_3$ positions is methyl group; and
A is $CH_2$—$CH(CH_3)$—or $CH$=$C(CH_3)$—.

5. The composition according to claim 4, wherein said nano-sized particle contains physiologically active agents therein.

6. The composition according to claim 5, wherein said physiologically active agent is at least one member selected from the group consisting of antibiotics, anti-tumor agent, anti-inflammatory agent, antipyretic, analgesia, anti-edema agent, anti-tussive agent, expectorant, depressant, muscle relaxant, antiepileptic, anti-ulcer agent, anti-melancholia agent, anti-allergy agent, cardiotonic agent, anti-arrhythmic agent, vasodilatin, hypotensive agent, anti-diabetic, homoeostasis agent, polypeptide, hormone; antioxidant; whitening agent, collagen synthesizing accelerant, membrane fortifier, moisturizing agent and an enzyme for removing a stratum corneum.

* * * * *